(12) United States Patent
Powers

(10) Patent No.: US 7,041,862 B2
(45) Date of Patent: May 9, 2006

(54) THERMAL CRACKING OF DIELS-ALDER ADDUCTS

(75) Inventor: Donald H. Powers, Pearland, TX (US)

(73) Assignee: Equistar Chemicals, LP, Houston, TX (US)

( * ) Notice: Subject to any disclaimer, the term of this patent is extended or adjusted under 35 U.S.C. 154(b) by 560 days.

(21) Appl. No.: 10/401,167

(22) Filed: Mar. 26, 2003

(65) Prior Publication Data
US 2004/0192988 A1 Sep. 30, 2004

(51) Int. Cl.
*C07C 13/00* (2006.01)
*C10G 9/00* (2006.01)

(52) U.S. Cl. .................................. 585/354; 208/125
(58) Field of Classification Search ................ 585/350; 208/125
See application file for complete search history.

(56) References Cited

U.S. PATENT DOCUMENTS

| 2,831,904 A | 4/1958 | Kreps ........................... 260/666 |
| 5,188,090 A | 2/1993 | Griggs ........................ 126/247 |
| 5,492,654 A | 2/1996 | Kozjuk et al. ................. 261/76 |
| 5,810,052 A | 9/1998 | Kozyuk ........................ 138/37 |

*Primary Examiner*—Thuan D Dang
(74) *Attorney, Agent, or Firm*—Roderick W. McDonald

(57) ABSTRACT

A method for thermally cracking Diels-Alder adducts and for altering organic streams containing Diels-Alder adducts using controlled cavitation conditions.

11 Claims, No Drawings

THERMAL CRACKING OF DIELS-ALDER ADDUCTS

BACKGROUND OF THE INVENTION

1. Field of the Invention

This invention relates to thermal cracking of Diels-Alder adducts to form a thermally cracked (cracked) product that contains at least the original compounds from which the adducts were formed, and recovering at least one of the thus formed original compounds from the cracked product.

More particularly this invention relates to the foregoing cracking process wherein the heat for the cracking is provided by controlled cavitation.

2. Description of the Prior Art

This invention is applicable to the thermal cracking of Diels-Alder reaction products in general. However, for sake of clarity and brevity this invention will largely be described with respect to cyclopentadiene (CPD), $C_5H_6$.

The Diels-Alder reaction is a useful reaction that is widely employed using conjugated dienes (the original diene compound) and an unsaturated compound (the original dieneophile compound) having a carbonyl group and/or a methylene group. It is an addition reaction in which the addition of an ethylenic group in the original dieneophile compound adds across the 1, 4 position of the original diene compound.

The Diels-Alder reaction is well known. It is a second order reaction that is carried out by simply bringing the two original compounds together in the presence or absence of a solvent at temperatures ranging from room temperature to about 390° F. The reaction is normally exothermic and yields in many situations are essentially quantitative.

CPD is a well-known chemical building block as is its dimer, dicyclopentadiene (DCPD), $C_{10}H_{12}$. Both are used extensively in industry.

DCPD exists in two stereoisomeric forms, endo and exo isomers, but the product predominantly used in commerce is the endo isomer. This invention is applicable to either isomer. DCPD (4, 7-methano-3a, 4, 7, 7a-tetrahydroindene) is the form in which CPD is normally commercially marketed.

CPD is a very robust chemical with wide applicability in industry. This is due to its conjugated double bonds coupled with an active methylene group. Thus, CPD can undergo a diene addition reaction with almost any unsaturated compound. CPD even forms adducts with itself and its oligomers as is demonstrated hereinbelow.

However, attention should first be drawn to the dimer DCPD. CPD oligomerizes spontaneously to DCPD at ordinary (room or ambient) temperature to DCPD without need of a catalyst or other aid. That is why CPD is normally sold in the form of DCPD. Above 212° F. CPD substantial and significant noncatalytic polymerization of CPD to its tri, tetra, and higher polymers can be achieved. The formation of DCPD from CPD, and the subsequent formation of higher oligomers and polymers thereof involves just a series of Diels-Alder reactions. For example, the dimer is formed by adding 1 mole of monomer to a second mole of monomer, while the trimer is formed by adding the monomer to the dimer, and so on.

It is convenient to employ CPD in the dimer form because the monomer and dimer are easy to separate by simple distillation, CPD having a boiling point of 106.7° F. and DCPD having a boiling point of 338° F. Cracking of DCPD can be achieved by boiling DCPD at ambient pressure. As DCPD boils at about 338° F., it cracks at a rate of about 36% per hour. By maintaining a distillation overhead temperature at from about 105° F. to about 108° F. essentially pure CPD can be obtained.

With its two conjugated double bonds CPD readily undergoes diene addition across its 1, 4 carbon atom position with a dieneophile. As a result of this reaction and the robustness of CPD as an original reactant compound, innumerable Diels-Alder adducts can be made from this single conjugated diene compound. For example, using just CPD as the conjugated diene in the reaction, the dieneophile that can be reacted with this single compound can be at least one of dibasic acids and derivatives such as chloromaleic anhydride, maleic anhydride, etc.; monobasic acids such as crotonic acid, methacrylic acid, etc.; aldehydes such as acrolein, crotonaldehyde, etc.; ketones such as propenyl methyl ketone, vinyl methyl ketone, etc.; ketene; vinyl compounds such as ethylene, styrene, vinyl acetate, allene, etc.; acetylenes such as acetylene, acetylenedicarbonitrile, etc.; quinones such as p-benzoquinone; nitroso compounds such as nitrosobenzene; and on and on. Hence the description of this invention in its broadest sense is cracking Diels-Alder adducts, with the detailed description of this invention being directed for sake of brevity largely to CPD and DCPD.

CPD is produced from a variety of thermal operations such as coal carbonization (tar, light oil, coke-oven gas) and thermal cracking of hydrocarbons (gas oil, naphtha, propane, ethane, and the like). CPD is recovered conventionally from other hydrocarbons by distilling such other hydrocarbons in a manner such that a distillate comprising $C_5$ hydrocarbons and lighter is formed. The distillate is heated at a temperature of about 212° F. to convert CPD to DCPD in a heat soaking operation that takes from about 5 to about 24 hours for reasons that will be explained hereinafter. The DCPD, which boils at a higher temperature than the unreacted hydrocarbons of the distillate, is recovered as distillation bottoms.

The dimer, DCPD, is the normal form in which CPD is made commercially available since CPD spontaneously reacts without help under ordinary conditions of temperature and pressure to form the dimer. CPD is formed by back cracking DCPD to CPD under elevated temperature, see U.S. Pat. No. 2,831,904 to Kreps.

Heretofore back cracking of DCPD to CPD to recover CPD has been carried out by heating the DCPD or DCPD containing stream at a temperature sufficient to back crack the DCPD, but, since DCPD is so reactive towards forming higher polymers, at the same time using a temperature and pressure sufficiently low to allow CPD to boil off while minimizing the formation of deposits of unwanted polymer(s) (polymer fouling). In addition to cracking DCPD by boiling same, vapor phase DCPD cracking can be employed. For example, DCPD can be vaporized and this vapor subjected to an elevated temperature of 600 to 700 degrees F. to thermally crack the DCPD to CPD. This high temperature vapor cracking process allows for a shorter cracking residence time.

Even when the back cracking temperature is kept low and a very long soaking time is tolerated, polymer fouling still occurs because when the reactive DCPD first hits a hot metal surface of the heat exchanger and furnace tubes employed in the back cracking process, gums (polymers) are formed on these hot surfaces and build up throughout even low temperature, long term cracking processes. Thus, unwanted polymers deposit on DCPD back cracking equipment is an omnipresent problem that hurts process efficiency and is costly to remove after the process is completed. Also, such unwanted polymers do not necessarily deposit in their entirety on hot equipment surfaces. Instead, some of these polymers can become dispersed in by-product streams of the process in question. When this occurs, because of its polymer content, the by-product stream can be severely degraded in its commercial value.

By this invention DCPD and many other Diels-Alder adducts can be back cracked to their original compounds without the need for extended soaking periods and without frequent and costly equipment cleaning to remove the polymer fouling currently endured by the prior art.

SUMMARY OF THE INVENTION

In accordance with this invention there is provided a method for back cracking Diels-Alder adducts to their original compounds by subjecting the adduct containing feedstock to controlled cavitation conditions which form a plurality of cavitation bubbles in the feedstock. These bubbles then implode thereby converting the mechanical energy employed in making the bubbles into heat. This heat is transferred to the feedstock in the location of the imploded bubbles. The cavitation conditions are controlled so that the heat generated by the imploding bubbles is sufficient to thermally back crack the adduct or adducts present at the location of the imploding bubbles to its/their original compounds used in forming the adduct(s) in the first place.

By this invention, and contrary to the prior art, the bulk or whole of the feedstock is not heated in its entirety to effect the desired back cracking. Instead, the bulk of the feedstock in this invention stays at a significantly lower temperature than is necessary to cause back cracking, thereby minimizing the potential for polymer fouling and by-product contamination. Further, the cracking heat in this invention is produced internally of the feedstock, i.e., the feedstock does not contact heated equipment surfaces and, therefore, unwanted polymer does not readily form, thereby minimizing, if not eliminating, both frequent costly equipment clean up and by-product streams that, due to their polymer content, must be downgraded, e.g., to fuel oil.

DETAILED DESCRIPTION OF THE INVENTION

In accordance with this invention, at least one Diels-Alder adduct which was previously formed from at least two original compounds, the conjugated diene and dienophile, is thermally cracked back to such original compounds using controlled cavitation to produce the heat required for such back cracking, to form a back cracked product, and separating at least one of said original compounds from the back cracked product.

This invention is applicable to any of the myriad Diels-Alder adducts available, some of which are described hereinabove, and which are susceptible to thermal cracking at least in part back to the original compounds from which the adduct was formed in the first place. Since CPD is marketed commercially in the form of DCPD, DCPD is a Diels-Alder adduct that is especially, but not solely, suited to back cracking pursuant to this invention. Other forms of DCPD are equally well suited to use in this invention. For example, adducts such as CPD isoprene, CPD piperylene, and the like (co-dimers) can be employed. Generally, conjugated dienes having from 4 to 8 carbon atoms per molecule can be employed to form a co-dimer with CPD. Dienophiles useful as an original compound also vary widely as shown in the partial list set forth hereinabove, any of which can be present in adducts processed in accordance with this invention.

The cavitation conditions useful in this invention can be produced by employing known cavitation devices, see U.S. Pat. Nos. 5,492,654 to Kozjuk et al. and 5,810,052 to Kozyuk. Cavitation devices useful in this invention produce a free disperse system using the well-known cavitation effect. Cavitation generators, due to the implosion of numerous bubbles mechanically formed in the interior of the body of fluid and/or liquid (fluid) being subjected to cavitation, imparts heat to such body of fluid without the use of heated metal surfaces. With prior art back cracking processes heat is transferred into a cooler liquid through the use of a significantly hotter metal surface. As explained above, this promotes polymer fouling. Also, the temperature differential between the hot metal surface and the cooler fluid can force certain impurities in the fluid, if present, to migrate to the hot metal surface and build up on that surface along with undesired polymer. With cavitation generators no hot heat transfer surfaces are employed. The metal surfaces in cavitation systems can be even cooler than the fluid being processed. The heat used for back cracking is formed in the interior of the fluid being processed due to the myriad of bubble dispersed therein. Thus, the heat is formed where it is needed, throughout the body of the fluid.

Accordingly, cracking heat is formed throughout the body or bulk of the fluid being processed without heating the entirety of that body to the cracking temperature. Since the back cracking of adducts is a first order chemical reaction, and, therefore, does not require a concentration of two separate molecules to proceed. Therefore, the back cracking of adducts proceeds readily without heating the entire body to the required cracking temperature. Thus, the bulk of the body stays cool. This minimizes second order chemical reactions that do require a concentration of two separate molecules at a reaction temperature to proceed such as the reformation of adduct in the body of fluid being processed. For example, as a molecule of DCPD in such a body back cracks to two molecules of CPD (original compounds from which the adduct DCPD was made) due to heat received from one or more imploding bubbles in the interior of that body and the two molecules separate from one another, if one of those molecules encounters another molecule of CPD it will try to form DCPD (a second order chemical reaction). However, if the temperature of the body of liquid is too low to trigger the second order reaction, such reaction will not occur and the two molecules of CPD will not combine to form a DCPD adduct. This is a substantial advantage for this invention which does not heat the entire body to the cracking temperature.

Thus, the process of this invention promotes back cracking, but at the same time minimizes both the reformation of adduct, and polymer fouling. An additional advantage with this invention is that with the use of microreactors (imploding bubbles) at very small locations within the body of the bulk fluid, the fluid stays well below the boiling point of the original compounds being reformed by the back cracking.

Cavitation in a body of fluid can be controlled in a manner such that it can be applied to heat the fluid to obtain back cracking of a variety of Diels-Alder adducts. Cavitation generators designed to create microscopic cavitation bubbles are commercially available. Such generators employ mechanical forces such as spinning discs that contain numerous cavities in a tightly enclosed area to convert mechanical energy into microscopic bubbles within the fluid being processed. These microscopic bubbles then promptly implode and release shock waves into the fluid. This converts mechanical energy that went into forming the bubbles into heat in the interior of the fluid without the use of heated metal surfaces that heat the entirety of the fluid. Thus, the heat necessary for effecting the desired adduct back cracking is provided, by way of this invention, internally of the feedstock and dispersed in localized micro volumes of the feedstock where each of the bubbles implodes. The cavitational forces created are capable of breaking down large gas bubbles into microscopic bubbles, and breaking down the Van der Waals attraction between liquid molecules.

The controlled cavitational conditions useful in this invention will vary widely due to the wide variety of adducts available for use in this invention, and will be readily determinable by one skilled in the art once the adduct(s) to be back cracked is identified. A degree of cavitation of at least 0.1 can be employed. When the adduct is DCPD or its co-dimers, cavitation conditions that provide heat from imploded bubbles sufficient to achieve, in the location of this imploded bubble a cracking temperature of at least about 300° F. at a pressure of from about atmospheric to about 20 psig can be used, with a temperature range of from about 400° F. to about 600° F. also being useful.

Controlled cavitation systems that are currently employed commercially in black liquor oxidation and heating, boiler feed mixing systems, various pulp and paper applications, and the like can be employed in this invention. The physical size of and absence of a flame source in such cavitational devices allows them to be added to existing facilities, e.g., as a pump around or feed for an existing distillation tower, without taking up large amounts of ground space. Cavitational devices useful in this invention can be operated in a batch mode in the same manner the prior art now depolymerizes DCPD to CPD using long soak periods. However, yet another advantage of this invention is that cavitation devices can also be operated in a semi-continuous or continuous mode and the desired back cracking still achieved.

The back cracked original compounds from which the back cracked adduct was originally formed can be separated from the back cracked product in many ways known in the art. A particularly useful separation technique is distillation.

When, for example, the adduct is DCPD, the cracked product contains, at least in part, a mixture of DCPD and CPD. By distilling this cracked product in a temperature range of from at least about the boiling point of CPD at the overhead of the distillation tower to not substantially greater than the boiling point of DCPD at the tower bottom under ambient pressure conditions, CPD is readily separated as overhead product while DCPD is separately removed as bottoms product.

Diels-Alder adducts can be present in various organic streams such as depentanizer bottoms in an olefin production plant, resin oils, and the like. For example, DCPD can be found in organic streams that are used as automotive gasoline blending components (gasoline grade stream), and, therefore will be added to the gasoline pool in one form or another. DCPD is not desirable in a gasoline grade stream because of its odor and its natural tendency to form gums (higher polymers). Removing CPD from such a stream by conventional thermal cracking of DCPD subjects the bulk of the stream to elevated cracking temperatures. This can degrade the gasoline quality of the stream by forming heavier hydrocarbons therein, even to the extent that it can no longer be used as a gasoline blending component. By the use of this invention, a gasoline grade stream containing DCPD can be upgraded by removal of at least some of such DCPD without risk of degrading such stream by employing conventional thermal cracking and its elevated temperature conditions. The CPD formed by this invention can be separated from such a gasoline grade stream by distillation without risk of degrading the stream because CPD has such a low boiling point.

Accordingly, organic streams containing at least one Diels-Alder adduct can be purified or otherwise altered by this invention by subjecting such a stream to controlled cavitation conditions to back crack at least one adduct to its original compounds from which such adduct was initially made followed by separation from such stream of at least one of such original compounds.

One or both of the original products so formed can be removed from the organic stream and recovered as a valuable product stream in its own right. For example, a gasoline grade stream that contains DCPD can have its DCPD content back cracked at least in part to CPD, and the CPD removed from the stream and recovered separately therefrom. Thereafter, the thus recovered CPD can be re-dimerized to form a high purity DCPD stream which has commercial value all of its own.

EXAMPLE 1

A resin oil hydrocarbon stream containing 40 weight percent (wt. %) DCPD based on the total weight of the stream is heated to a temperature of about 200° F. and passed into a controlled cavitation device described in U.S. Pat. No. 5,492,654 to form a free disperse system in said DCPD containing stream that contains a plurality of microbubbles. After their formation in such device, the bubbles implode and thereby generate shock waves that heat DCPD in the location of the bubble implosion to a cracking temperature in the range of from about 400° F. to about 600° F. thereby thermally cracking at least some DCPD in such location to two molecules of CPD, the original compounds from which the DCPD was initially formed.

A fluid mixture of liquid DCPD and gaseous CPD is removed from the cavitation generator system and subjected to distillation in a tower whose overhead temperature is about 106° F. and whose bottom temperature is not greater than about 338° F., whereby CPD is recovered overhead of the tower. The thus recovered CPD is re-dimerized to form a high purity DCPD stream.

DCPD recovered as bottoms product is recycled to the cavitation generator system as co-feed therefore to back crack at least part of same.

EXAMPLE 2

Example 1 is repeated except that a resin oil hydrocarbon stream containing 80 wt. % DCPD based on the total weight of the stream is employed as the feedstock.

The CPD recovered overhead of the tower is then separately employed to form other chemical entities.

I claim:

1. A method for altering an organic stream that contains at least one Diels-Alder adduct formed from at least two original compounds comprising subjecting said stream to controlled cavitation conditions to form a plurality of cavitation bubbles in said stream under conditions in which said bubbles implode and thereby heat said stream in the location of said imploded bubbles to a temperature sufficient to crack said adduct back to its original compounds used in forming said adduct, and removing at least one of said original compounds from said stream.

2. A method for thermally cracking at least one Diels-Alder adduct, said adduct having been originally formed from at least one conjugated diene compound and at least one unsaturated compound having at least one of a carbonyl group and a methylene group, said method comprising providing a feedstock containing said at least one adduct, subjecting said feedstock to controlled cavitation conditions wherein a plurality of cavitation bubbles are formed in said feedstock which bubbles implode after formation of same and thereby heat said feedstock in the location of said imploded bubbles to a temperature sufficient to thermally crack said at least one adduct at least in part, said at least one adduct being cracked into said original compounds, and recovering at least one of said original compounds from said cracked feedstock.

3. The method of claim 2 wherein said at least one adduct is at least one of dicyclopentadiene and co-dimers of dicyclopentadiene.

4. The method of claim 3 wherein said co-dimers are selected from the group consisting of cyclopentadiene isoprene, cyclopentadiene piperylene, and mixtures thereof.

5. The method of claim 3 wherein said feedstock is subjected to cavitation conditions that provide heat within said feedstock in the location of said imploded bubbles to a cracking temperature of at least about 300° F. at a pressure of from about atmospheric to about 20 psig.

6. The method of claim 5 wherein said cracking temperature is from about 400° F. to about 600° F.

7. The method of claim 2 wherein the degree of cavitation is at least 0.1.

8. The method of claim 2 wherein said at least one original compound is recovered from said cracked feedstock by distillation.

9. The method of claim 3 wherein said at least one original compound is recovered by distilling said cracked feedstock in a temperature range of from at least about the boiling point of cyclopentadiene at the overhead to not substantially greater than the boiling point of dicyclopentadiene at the bottoms and under ambient pressure.

10. The method of claim 5 wherein said adduct is dicyclopentadiene, and said recovered original compound is cyclopentadiene.

11. The method of claim 10 wherein said cyclopentadiene is recovered by distilling said cracked feedstock in a temperature range of from at least about the boiling point of cyclopentadiene at the overhead to not substantially greater than the boiling point of dicyclopentadiene at the bottoms, and under ambient pressure.

* * * * *

UNITED STATES PATENT AND TRADEMARK OFFICE
CERTIFICATE OF CORRECTION

PATENT NO.       : 7,041,862 B2
APPLICATION NO.  : 10/401167
DATED            : May 9, 2006
INVENTOR(S)      : Donald H. Powers It is certified that error appears in the above-identified patent and that said Letters Patent is hereby corrected as shown below:

On the Title Page,
PLEASE CORRECT THE SPELLING OF THE ATTORNEY'S NAME Item (74).

THE CORRECT SPELLING IS AS FOLLOWS:   Roderick W. MacDonald

Signed and Sealed this

Eighth Day of August, 2006

JON W. DUDAS
*Director of the United States Patent and Trademark Office*